Figure 1:
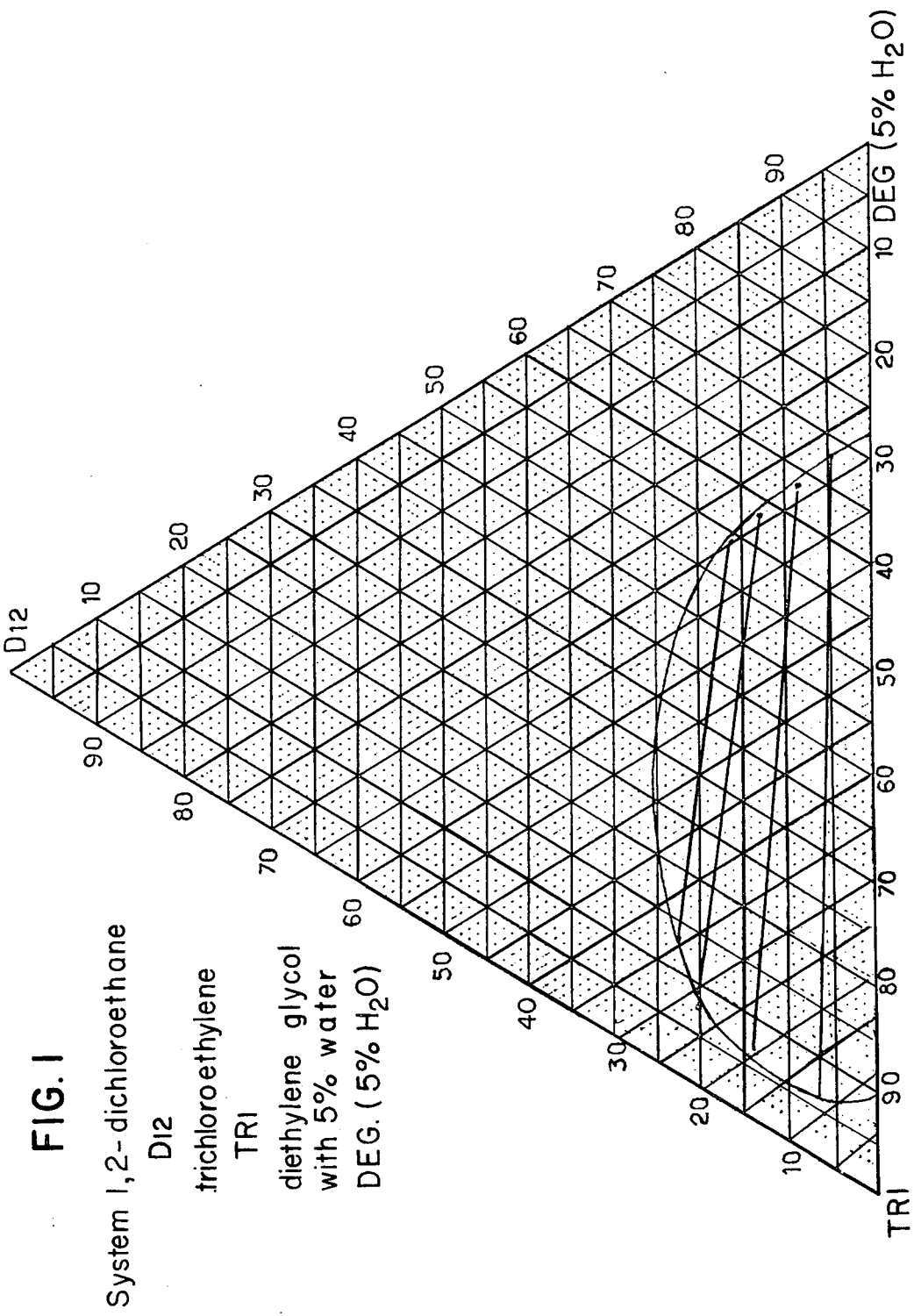

United States Patent [19]

Helgorsky

[11] 4,031,148

[45] June 21, 1977

[54] METHOD OF SEPARATING CHLORINATED ALIPHATIC HYDROCARBONS FROM MIXTURES THEREOF BY LIQUID-LIQUID EXTRACTION

[75] Inventor: Jacques Helgorsky, Eaubonne, France

[73] Assignee: Rhone-Poulenc Industries, Paris, France

[22] Filed: Mar. 11, 1976

[21] Appl. No.: 666,050

Related U.S. Application Data

[63] Continuation-in-part of Ser. No. 437,516, Jan. 28, 1974, abandoned.

[30] Foreign Application Priority Data

Jan. 30, 1973 France .............................. 73.03179

[52] U.S. Cl. ............................................. 260/652 P
[51] Int. Cl.² ........................................ C07C 17/38
[58] Field of Search ................ 260/652 P; 437/516

[56] References Cited

UNITED STATES PATENTS

| | | |
|---|---|---|
| 2,275,151 | 3/1942 | Kimberlin .................... 260/652 P |
| 2,357,028 | 8/1944 | Shiras et al. .................. 260/652 P |
| 2,456,184 | 12/1948 | Greenwald ..................... 260/654 S |
| 3,113,079 | 12/1963 | Bergeron et al. .............. 260/652 P |
| 3,197,941 | 8/1965 | Colton et al. .................. 260/652 P |
| 3,427,358 | 2/1969 | Washall .......................... 260/652 P |
| 3,658,657 | 4/1972 | Bursack et al. ................ 260/652 P |
| 3,658,658 | 4/1972 | Bursack et al. ................ 260/652 P |

*Primary Examiner*—D. Horwitz
*Attorney, Agent, or Firm*—McDougall, Hersh & Scott

[57] ABSTRACT

A method of partially or totally separating $C_1$ to $C_3$ chlorinated aliphatic hydrocarbons from mixtures of at least two of such compounds; a liquid-liquid operation is carried out on such mixtures in the presence of one or more extraction agents having at least partial water-miscibility, the extraction agents being selected from the group of aprotic polar solvents, from the group of polyhydric alcohols, more particularly $C_2$ to $C_7$ saturated aliphatic polyhydric alcohols, $C_4$ to $C_8$ polyglycols, and glycol monoethers, more particularly $C_3$ to $C_8$ saturated aliphatic monoethers and the use of this process for the separation of mixtures comprising or essentially consisting of 1,2-dichloroethane and trichloroethylene.

7 Claims, 5 Drawing Figures

Selectivity curve
Extraction by DEG (10% $H_2O$)

METHOD OF SEPARATING CHLORINATED ALIPHATIC HYDROCARBONS FROM MIXTURES THEREOF BY LIQUID-LIQUID EXTRACTION

This is a continuation-in-part of my copending application Ser. No. 437,516, filed Jan. 28, 1974, now abandoned and entitled "Method of Separating Chlorinated Aliphatic Hydrocarbons from Mixtures Thereof by Liquid-Liquid Extraction".

The present invention relates to a method of partially or totally separating $C_1$ to $C_3$ chlorinated aliphatic hydrocarbons from mixtures of at least two of such compounds, by liquid-liquid extraction.

The separation of mixtures of certain chlorinated aliphatic hydrocarbons having up to 3 carbon atoms and more particularly, binary mixtures of trichloroethylene and 1,2-dichloroethane, perchloroethylene and 1,1,2-trichloroethane, carbontetrachloride and 1,2-dichloroethane, and 1,1,1-trichloroethane 1,2-dichloroethane, is very difficult to carry out of conventional fractionated distillation, either because of the formation of an azeotrope or because of the low relative volatility of the substances involved.

For example, the separation of trichloroethylene from 1,2-dichloroethane is extremely important for producing vinyl-chloride and $C_2$ and/or $C_1$ chlorinated aliphatic hydrocarbons, as solvents. However, it is known that 1,2-dichloroethane and trichloroethylene have boiling points which are very close (83.65° and 86.2° C respectively), and that they form an azeotrope with 62 molar percent of 1,2-dichloroethane, distilling at 82.2 C at atmospheric pressure. Because of this, it is impossible, by conventional distillation, to separate any mixtures of these two compounds into pure substances. It is also not possible to envisage a process of distillation in two columns operating at different pressures, as the azeotrope is of a virtually constant composition, dependent on pressure.

It is also known that, for some mixtures which are difficult to separate by distillation, it is possible to find a solvent or solvents, which will be referred to hereinafter by the term "extraction agents", which are capable of preferentially extracting one of the constituents from the mixture, while being immiscible or having only a low degree of miscibility with the second constituent. In this case, it is possible to use the process which is well known under the name liquid-liquid extraction, which has been used for separating aromatic hydrocarbons and/or paraffinic hydrocarbons.

The extraction agents which are capable of effecting the separation operations obviously vary according to the nature of the mixtures to be separated. However, it is virtually impossible to foresee the extraction agent which will make it possible to carry out any separation operation of given substances.

The applicants have found that extraction agents selected from so-called polar aprotic solvents, and protondonor and/or proton-acceptor solvents make it possible, in an easy and highly satisfactory manner, to carry out separation operations in the group of $C_1$ to $C_3$ chlorinated aliphatic hydrocarbons.

In accordance with the method of the invention, a liquid-liquid extraction operation is carried out on mixtures to be separated in the presence of one or more extraction agents having at least partial water-miscibility; the extraction agents are selected from the group of polar aprotic solvents, more particularly those which are $C_1$ to $C_6$ saturated aliphatic, polyhydric alcohols, more particularly those which are $C_2$ to $C_7$ saturated aliphatic, $C_4$ to $C_8$ polyglycols and glycol monoethers and in particular those which are $C_3$ to $C_8$ saturated aliphatic.

By way of examples to illustrate but in no way limit the present invention, the following compounds belonging to the above-mentioned classes may be mentioned:

Dimethylsulfoxide, dimethylformamide, sulfolane and its $C_1$ and $C_2$ alkylated derivatives, N-methylpyrrolidone, hexamethylphosphotriamide; propylene carbonate and ethylene carbonate, which are representative of the group of polar aprotic solvents; ethylene glycol, propylene glycol and glycerol, which are representative of the polyhydric alcohols; diethylene glycol, triethylene glycol, tetraethylene glycol, dipropylene glycol, and polyethylene and polypropylene glycols having a molecular weight of less than 600, which are representative of the polyglycols.

Furfuryl alcohol, tetrahydrofurfuryl alcohol, 2-methoxy ethanol, 2-ethoxy ethanol, 2-butoxy ethanol, 2-(2-methoxy ethoxy) ethanol, 2-(2-ethoxy ethoxy) ethanol, 2-(2-botoxy ethoxy) ethanol, which are representative of the glycol monoethers.

Although they are particularly effective as regards separation, the extraction agents of the present invention are often excessively soluble in $C_1$ to $C_3$ chlorinated aliphatic hydrocarbons, which makes it difficult to use them in liquid-liquid extraction operations.

In accordance with a particular embodiment of the invention, water is added to the extraction agents, which greatly limits their solubility in at least one of the chlorinated hydrocarbons and thus promotes conditions for separation.

The applicants have in fact observed that, in the case of a mixture of $C_1$ to $C_3$ chlorinated aliphatic hydrocarbons, these extraction agents, when mixed with water, made it possible to produce a homogenous phase which was only slightly miscible with at least one of the chlorinated hydrocarbons, but which had nonetheless retained the property of extracting to a greater or lesser extent the other chlorinated hydrocarbon or hydrocarbons of the initial mixture.

According to the invention, the amount of water necessary for producing this phenomenon, which is referred to as "demixing", depends on several factors such as the nature of the extraction agent and the chlorinated hydrocarbons to be separated, their relative proportions, and temperature. Generally, the proportion of water can vary from 0 to 50% by weight.

The applicants also found that the degree of extraction of the $C_1$ to $C_3$ chlorinated aliphatic hydrocarbons increased in proportion as the amount of water in the extraction agent was reduced, but that separation thereof was rendered less efficient.

The method of the invention can be used in general for mixtures in any proportions of $C_1$ to $C_3$ chlorinated aliphatic hydrocarbons.

The following non-limiting list of substances can be identified as normal constituents of such mixtures: $CCl_4$, $CHCl_3$, $C_2H_5Cl$, $C_2H_4Cl_2$, $C_2H_3Cl_3$, $C_2H_2Cl_4$, $C_2HCl_5$, $C_2Cl_6$, $C_2HCl_3$, $C_2H_3Cl$, $C_2H_2Cl_2$, $C_2Cl_4$ and/or $C_3H_6Cl_2$.

It can happen that these mixtures also contain, besides the $C_1$ to $C_3$ chlorinated aliphatic hydrocarbons, other compounds such as, inter alia, $CCl_3$–$CHO$, $HCl$, $C_2H_4$, $C_2H_2$, $C_2H_6$, butadiene, chlorobutadienes, chlorobenzenes and chlorobutanes. In such event, these constituents may be separated by any suitable means such as distillation, the method of the invention then being applied only to the mixtures which are difficult to separate.

The following can be mentioned, inter alia, as particular examples of mixtures which are difficult to separate, besides the mixture comprising or essentially consisting of 1,2-dichloroethane and trichloroethylene; the mixtures of perchloroethylene and 1,1,2-trichloroethane, carbontetrachloride and 1,2-dichloroethane, and 1,1,1-trichloroethane and 1,2-dichloroethane.

According to the invention, temperature is an important factor in the operation of separation by liquid-liquid extraction of chlorinated aliphatic hydrocarbons from the mixture thereof. Temperature variation causes a modification in the thermodynamic properties of the systems, and in particular, the partition coefficients and the separation factors in respect of the chlorinated hydrocarbons.

Although it is possible to operate within a large temperature range, ranging for example from ambient temperature to temperatures adjacent to but below the boiling temperature of the most volatile substance in the mixture, for practical reasons it is preferred that operation be carried out in the region of ambient temperature.

Moreover, under the operating conditions of the method of the invention, a variation in pressure about atmospheric pressure has little influence on the properties of the system and is of little practical interest.

A particular aspect of the invention being the separation of 1,2-dichloroethane (D12) and trichloroethylene (Tri), reference will hereinafter be made to this separation operation, which is particularly difficult but which is important in industrial practice.

Thus, for a mixture of these two chlorinated hydrocarbons, in approximately equal-weight amounts, it was found that the amount of water necessary to produce the demixing phenomenon is at least 5% by weight when diethylene glycol is used as the extraction agent. In contrast, in the case of ethylene glycol, it is not necessary to add water to produce a clear separation between the phases.

In order to compare the efficiency of different extraction agents of the invention, the selection was limited to some typical alcohols, polyhydric alcohols and polyglycols as mentioned above, and their behavior in dependence on their water content was studied. Table 1 hereinafter gives a certain number of their characteristics, as indicated by the following notations:

$P_{D12}$ is the partition coefficient as regards 1,2-dichloroethane; it is represented by the ratio between the fraction by weight of 1,2-dichloroethane in the hydroalcohol phase and the fraction by weight of 1,2-dichloroethane in the chlorinated hydrocarbon phase (which is the heavy phase in every case).

$P_{TRI}$ is the partition coefficient in respect of trichloroethylene; it is represented by the ratio between the fraction by weight of trichloroethylene in the hydroalcohol phase and the fraction by weight of trichloroethylene in the chlorinated hydrocarbon phase (which is the heavy phase in every case).

$F_{D12/TRI}$ is the separation factor as between 1,2-dichloroethane and trichloroethylene; it is represented by the ratio $P_{D12}/P_{TRI}$.

$S_{D12, TRI}$ is the solvent capacity of the alcohol; it represents the content by weight of 1,2-dichloroethane and/or trichloroethylene in the alcohol phase.

TABLE 1

EXTRACTION OPERATION ON A MIXTURE HAVING THE FOLLOWING OVERALL COMPOSITION BY WEIGHT:

- 1,2-dichloroethane = 20%
- Trichloroethylene = 50%
- Alcohol = 27%
- Water = 3%

| ALCOHOL | $P_{D12}$ | $F_{D12/TRI}$ | $S_{D12/TRI}$ |
|---|---|---|---|
| Ethylene glycol | 0.098 | 3.3 | 4.6 |
| Propylene glycol | 0.20 | 2.0 | 12.6 |
| Diethylene glycol | 0.36 | 1.9 | 19.4 |
| Triethylene glycol | 0.66 | 2.3 | 37.7 |
| Tetraethylene glycol | 0.69 | 1.7 | 33.8 |
| Methyl alcohol | 0.63 | 1.9 | 40 |

This table shows that, with equal water content, the alcohols which best extract 1,2-dichloroethane and trichloroethylene ($P_{D12}$, $P_{TRI}$ and $S_{D12, TRI}$ are high) separate them least well ($F_{D12/TRI}$ are low) and vice versa. It is found that diethylene glycol is one of the extraction agents which affords the most attractive compromise from the point of view of economy.

Table 2 below shows the influence of the water content in diethylene glycol on the extraction of 1,2-dichloroethane and trichloroethylene.

TABLE 2

EXTRACTION OPERATION ON A MIXTURE HAVING THE FOLLOWING OVERALL COMPOSITION BY WEIGHT:

- 1,2-dichloroethane = 20%
- Trichloroethylene = 50%
- Diethylene glycol, water = 30%

| Content by weight of water in the diethylene glycol water mixture | $P_{D12}$ | $F_{D12/TRI}$ |
|---|---|---|
| 5% | 0.62 | 1.5 |
| 10% | 0.36 | 1.9 |
| 15% | 0.23 | 2.1 |
| 20% | 0.13 | 2.5 |
| 30% | 0.08 | 3.0 |
| 50% | 0.027 | 5.0 |
| 80% | 0.016 | 6.4 |
| 100% | 0.010 | 9.2 |

It is found that increasing the water content causes greater reduction of the partition coefficients (for example $P_{D12}$) than it increases the separation factors ($F_{D12/TRI}$). The most attractive range is from 5 to 15% of water. Obviously the range of preferred operating conditions is to be determined experimentally, as it varies according to the extraction agent envisaged.

Extraction agent and water have been studied in detail for the system comprising 1,2-dichloroethane, trichloroethylene extraction and illustrated in the form of ternary diagram: 1,2-dichloroethane (D12), trichloroethylene (TRI), diethylene glycol + water, because of the very low degree of solubility of water and diethylene glycol in the chlorinated solvents.

Figure 2:
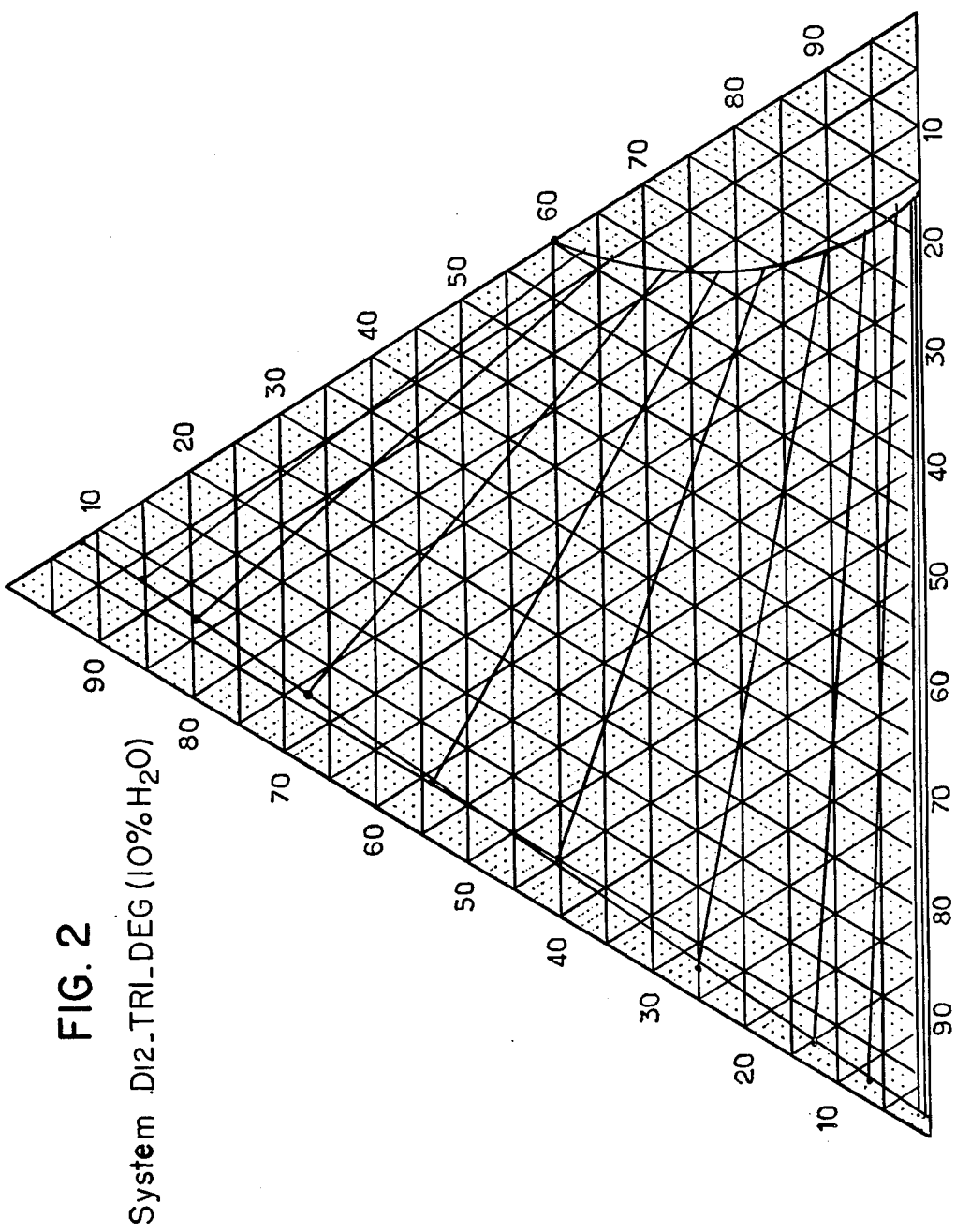

FIGS. 1 and 2 of the accompanying drawings show the ternary systems with diethylene glycol, containing respectively 5 and 10% of water at a temperature of 25° C and at atmospheric pressure.

It will be seen that for a water content of 5%, a so-called "closed" diagram is produced, permitting the production of very pure trichloroethylene but not permitting advanced purification of 1,2-dichloroethane. In contrast, the system with 10% water is "open", and can therefore be used for advanced purification of 1,2-dichloroethane with respect to the trichloroethylene.

Figure 3:
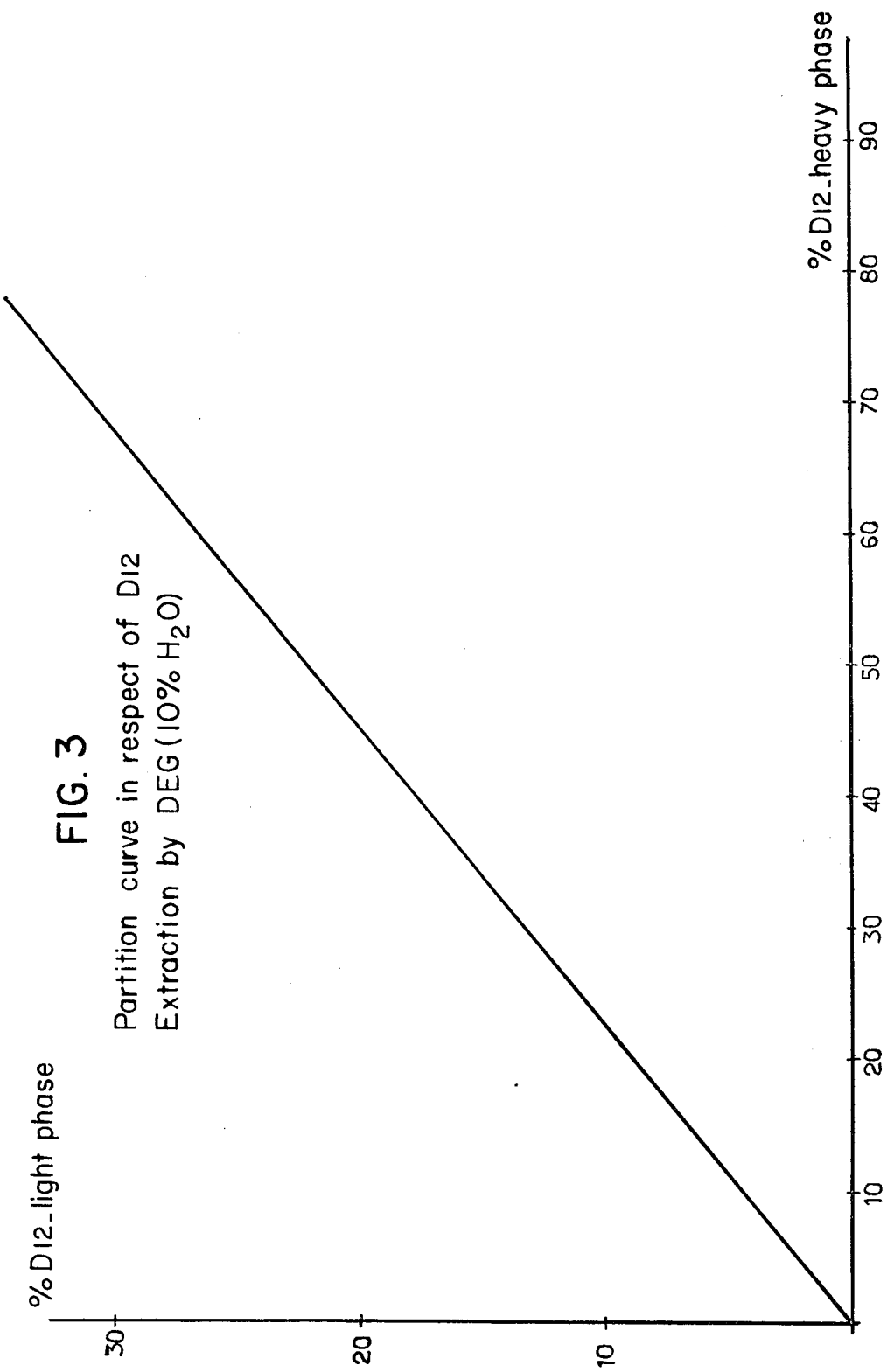
Figure 4:
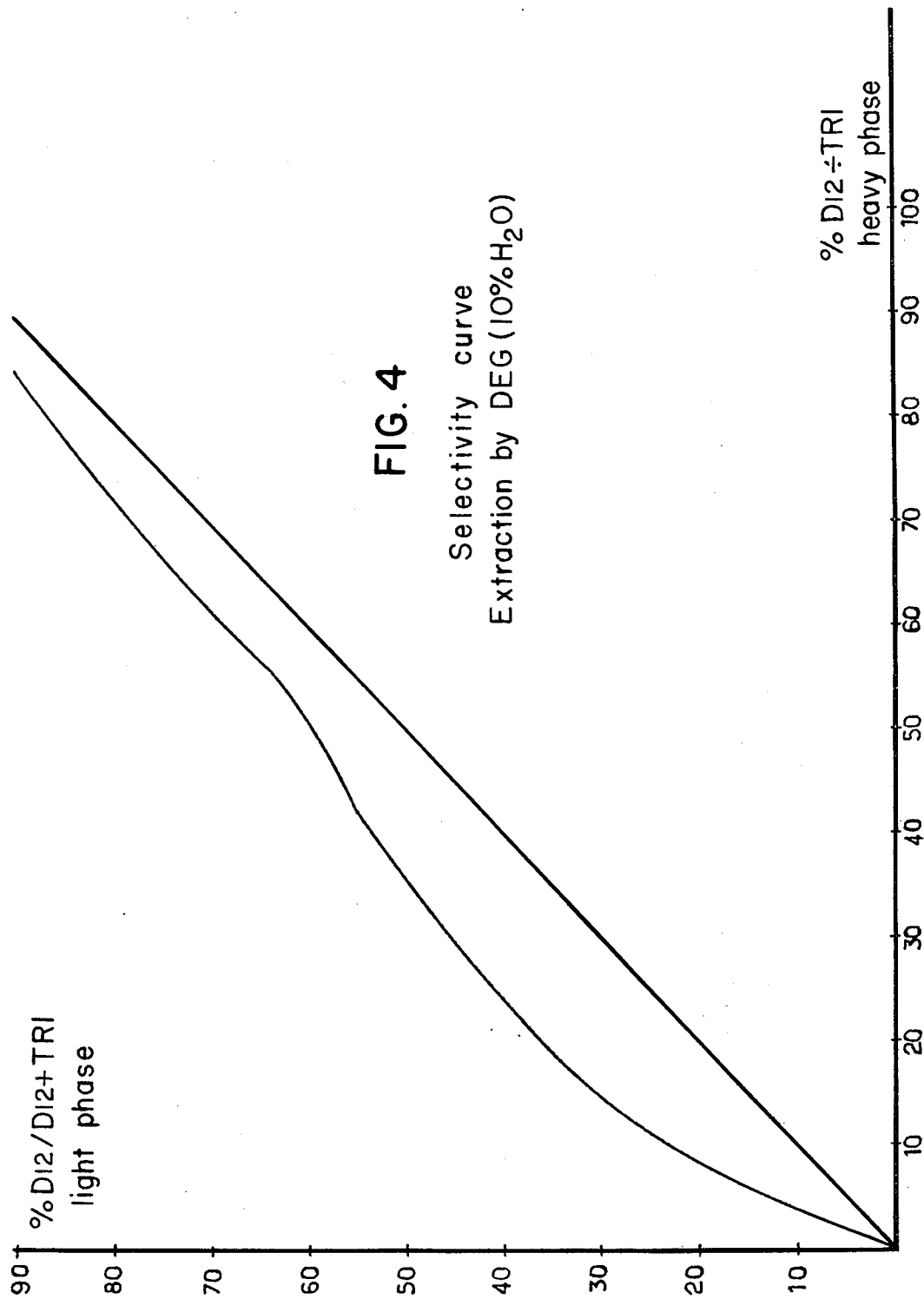

FIG. 3 shows the partition curve and FIG. 4 shows the selectivity curve of 1,2-dichloroethane and trichloroethylene for the ternary system with diethylene glycol containing 10% of water. It will be seen that the partition coefficient in respect of 1,2-dichloroethane remains substantially constant, in dependence on the content of 1,2-dichloroethane in the heavy phase (chlorinated substances), whereas the degree of selectivity (expressed by $F_{D12/TRI}$) decreases with the proportion of 1,2-dichloroethane in the heavy phase. The preparation of very pure trichloroethylene in a counter-flow apparatus is therefore easier than preparing very pure 1,2-dichloroethane. It is noted in FIG. 4 that there is a relatively abrupt drop in selectivity at the level of the amount corresponding to the azeotrope. This shows that the azeotrope has not been totally dissociated by the presence of the diethylene glycol.

FIGS. 1 to 4 make it possible to calculate the conditions for separation by methods well known to the man skilled in the art. It is thus possible to define and optimize the operating conditions of a counter-flow contact apparatus supplying on the one hand a heavy phase, which will be referred to as the "refinate", and which comprises trichloroethylene which is purified in comparison with the 1,2-dichloroethane, but which contains a small amount of extraction agent and water, and, on the other hand, a light phase which will be referred to as the "extract" and which comprises the extraction agent, water and the 1,2-dichloroethane which has been purified in comparison with the trichloroethylene.

In general, the trichloroethylene should contain only a very small amount of impurities for commercial applications thereof. The extraction agent, which is present in the trace state in the trichloroethylene, can easily be re-extracted by water in accordance with the invention, and then recovered by simple distillation. The recovered re-extraction water and extraction agent are recycled to the installation. The trichloroethylene is dried by conventional means and can thus be made commerically available.

The extract, which is enriched with 1,2-dichloroethane, is subjected to a so-called "regeneration" operation, for recovering on the one hand the 1,2-dichloroethane and on the other hand the aqueous extraction agent which is recycled into the main contacting apparatus.

Regeneration can, in most cases, easily be carried out by distillation, taking into account the large difference between the boiling temperatures of the aqueous extraction agent (130° C for diethylene glycol containing 10% water) and that of the 1,2-dichloroethane (83.5° C).

In accordance with one embodiment of the present invention, there is effected a regeneration operation which is more reliable (which is carried out at ambient temperature, therefore without the danger of degradation of the extraction agent) and which is more economical, than conventional distillation. It comprises using a so-called regeneration solvent which extracts the 1,2-dichloroethane without extracting the aqueous extraction agent or the water. Paraffinic hydrocarbons, which are liquid under the operating conditions, have this property. For example, it is possible to use, at ambient temperature and at atmospheric pressure, a paraffinic hydrocarbon having a low boiling point, such as pentane (36° C), or a hydrocarbon having a high boiling point, such as dodecane (214.5° C); it is possible to use, above a temperature of 51° C and at atmospheric pressure, n-tetracosane having a boiling point of 324.1° C. These regeneration solvents provide for easy re-extraction of the 1,2-dichloroethane which is then separated by distillation from the pentane in the first case or the 1,2-dichloroethane itself in the other two cases. In every case, this distillation operation is by far more economical than direct distillation on the extract, which requires heating a substantial amount of the aqueous extraction agent, which has a high specific heat.

Figure 5:
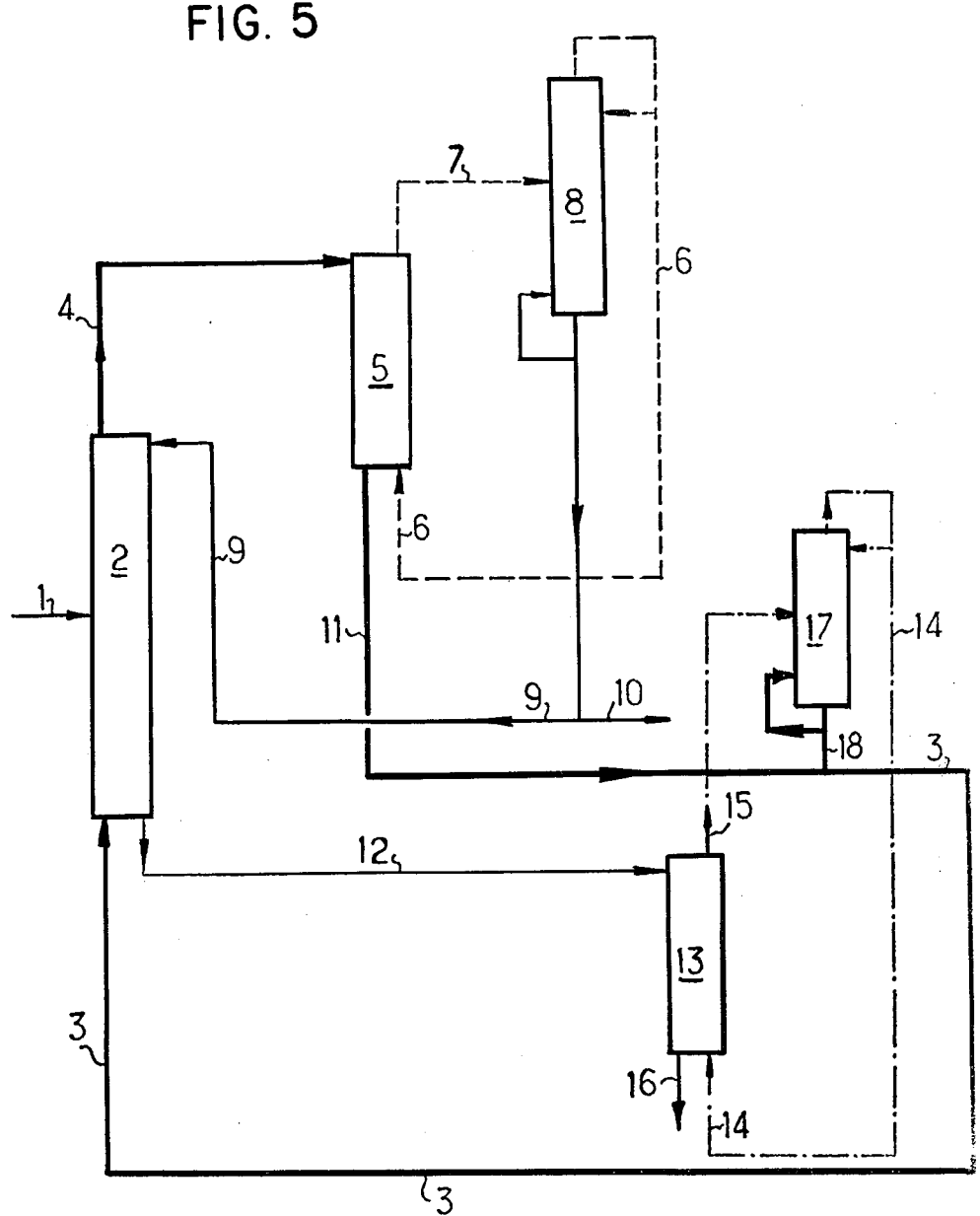

FIG. 5 diagrammatically shows the essential parts of an installation for separating mixtures of chlorinated aliphatic hydrocarbons according to the invention. Operation of the installation is hereinafter described for a binary mixture of chlorinated aliphatic hydrocarbons A and B.

A mixture of A and B is introduced from line 1 into the middle part of the multi-stage contact apparatus 2. Aqueous extraction agent is also introduced from line 3 at the bottom of the contacting apparatus. The extract which has been enriched with A is passed through line 4 to one of the ends of the multi-stage regeneration contacting apparatus 5 which at its other end receives a regeneration solvent from line 6 which re-extracts A, is discharged from the contacting apparatus (line 7) and is injected into a distillation column 8 which separates on the one hand the solvent (line 6) which is recycled to the apparatus 5, and on the other hand, the purified hydrocarbon A of which a part (line 9) is reintroduced at the top of the apparatus 2 in which the chlorinated hydrocarbon B is flowing down. The other part (line 10) constitutes the production of purified hydrocarbon A.

The regenerated solvent (line 11) is recycled to the apparatus 2.

The "refinate" of the extraction operation (line 12) which essentially comprises B is injected into a multi-stage purification contacting apparatus 13 in which a water washing operation (line 14) extracts the extraction agent (line 15); purified hydrocarbon B is collected (line 16). The mixture comprising extraction agent and water (line 15) is injected into a distillation column which separates on the one hand the aqueous extraction agent (line 18) which is recycled to the apparatus 2, and on the other hand, the water (line 14) which is reinjected into the apparatus 13.

The aim of the following example is to illustrate the various aspects of the invention, using the installation shown in FIG. 5, but it is not to be considered as limiting the scope of the invention.

EXAMPLE

The feed flow 1 comprising an equal-weight mixture of 1,2-dichloroethane and trichloroethylene is injected at a flow rate of 1 kg/hour in the thirteenth stage of an extraction column 2 comprising 20 theoretical stages.

The extraction agent (line 3) is a mixture of diethylene glycol and water (10% by weight of water) which is injected in the first stage of the extraction column 2 at a flow rate of 5.72 kg/h.

The "refinate" (line 12), discharged from stage 1 at a flow rate of 0.46 kg/hour, which contains:
   trichloroethylene: 98.5%
   1,2-dichloroethane: 0.02%
   diethylene glycol: 1.45% water: 0.024%
is injected at the top of an extraction column 13 having five theoretical stages; at the other end water is injected (line 14) at a flow rate of 20 g/h.

Taken off at the first stage of the column 13 is purified trichloroethylene (line 16) which now contains nothing more in the way of impurities than 200 parts per million by weight (ppm) of 1,2-dichloroethane, 15 ppm of diethylene glycol and 240 ppm of water.

The extract, discharged from the twentieth stage of column 2 (line 4) at a flow rate of 9.19 kg/h, is enriched with 1,2-dichloroethane, and its composition by weight is as follows:

diethylene glycol 55.4%
water: 6.1%
1,2-dichloroethane: 35%
trichloroethylene: 3.5%

The flow 4 is injected at the top of the regeneration column 5 which comprises five theoretical stages, while at the bottom thereof is introduced a flow 6 of pentane, at a flow rate of 5.7 kg/h. The pentane having extracted almost all the 1,2-dichloroethane (line 6), has the following composition by weight:

pentane 61.5%
1,2-dichloroethane: 35%
trichloroethylene: 3.5%

The pentane is separated by distillation (line 6) in the column 8 and is recycled to the column 5.

The fraction which is enriched with 1,2-dichloroethane, issuing from the bottom end of the distillation column 8, has the following composition by weight:

1,2-dichloroethane: 90%
trichloroethylene: 10%

It is partially recycled (line 9) at a flow rate of 2.93 kg/h to the top of the column 2. The mixture of diethylene glycol and water (line 11) issuing from the regeneration column 5 contains very small traces of 1,2-dichloroethane and can therefore be recycled to the bottom of the column 2.

The above-described installation makes it possible to produce trichloroethylene in a state of purity of 99.98% (by weight), in a yield of 92% (by weight) from an initial equal-weight mixture of 1,2-dichloroethane and trichloroethylene.

It is obvious that these conditions are not limitative, and that it is possible to vary them depending on the desired specifications.

Thus, it is possible to carry out separation operations under widely varying conditions of 1,2-dichloroethane and trichloroethylene. Depending on the state of purity in which trichloroethylene and ',2-dichloroethane are to be produced, it is possible to use an extraction agent other than diethylene glycol, selected from those defined above. Likewise, operation can be with amounts of water which vary according to the nature of the extraction agent selected.

In addition, the amount of extraction agent to be used can be selected within certain limits, for a given amount of the mixture or chlorinated aliphatic hydrocarbons to be separated, provided that use is made of an extractor apparatus having a suitable number of theoretical stages.

I claim:

1. A method of at least partial separation of mixtures of at least two $C_1$ to $C_3$ chlorinated aliphatic hydrocarbons selected from the group consisting of $CCl_4$, $CHCl_3$, $C_2H_5Cl$, $C_2H_4Cl_2$, $C_2H_3Cl_3$, $C_2H_2Cl_4$, $C_2HCl_5$, $C_2Cl_6$, $C_2H_3Cl$, $C_2H_2Cl_2$, $C_2Cl_4$, $C_3H_6Cl_2$, and $C_2HCl_3$, comprising liquid-liquid extraction on such mixtures, in the presence of one or more extraction agents having at least partial water-miscibility, and adding from 0 to 50% by weight of water, the extraction agents being selected from the group consisting of dimethylsulfoxide, dimethylformamide, sulfolane, $C_1$ and $C_2$ alkylated derivatives of sulfolane, N-methylpyrrolidone, hexamethylphosphotriamide, propylene carbonate, ethylene carbonate, ethylene glycol, propylene glycol, glycerol, diethylene glycol, triethylene glycol, tetraethylene glycol, dipropylene glycol, polyethylene and polypropylene glycols having a molecular weight of less than 600, furfuryl alcohol, tetrahydrofurfuryl alcohol, 2-methoxy ethanol, 2-ethoxy ethanol, 2-butoxy ethanol, 2-(2-methoxy ethoxy) ethanol, 2-(2-ethoxy ethoxy) ethanol, and 2-(2-butoxy ethoxy)

2. A method according to claim 1 characterized in that the separation is carried out on the mixture of 1,2-dichloroethane and trichloroethylene to extract 1,2-dichloroethane from trichloroethylene which remains in the raffinate.

3. A method according to claim 1 characterized in that the separation is carried out on mixtures of perchloroethylene and 1,1,2-trichloroethane.

4. A method according to claim 1 characterized in that the separation is carried out on mixtures of carbontetrachloride and 1,2-dichloroethane.

5. A method according to claim 1 characterized in that the separation is carried out on mixtures of 1,1,1-trichloroethane and 1,2-dichloroethane.

6. A method according to claim 1 characterized in that the separation temperature is between ambient temperature and the temperature which is close to but below the boiling temperature of the most volatile substance of the mixture.

7. A method according to claim 2, characterized in that the extract which is enriched with 1,2-dichloroethane is subjected to regeneration by means of a solvent which extracts only 1,2-dichloroethane, and in which the solvent is selected from the group of paraffinic hydrocarbons which are liquid under the operating conditions.

* * * * *

UNITED STATES PATENT OFFICE
CERTIFICATE OF CORRECTION

Patent No. 4,031,148           Dated June 21, 1977

Inventor(s) Jacques Helgorsky

It is certified that error appears in the above-identified patent and that said Letters Patent are hereby corrected as shown below:

column 1, line 21, change "of" to --by--.

column 8, line 30, at end of line, add --ethanol--.

Signed and Sealed this

Twentieth Day of September 1977

[SEAL]

Attest:

RUTH C. MASON  
Attesting Officer

LUTRELLE F. PARKER  
Acting Commissioner of Patents and Trademarks